(12) United States Patent
Levorse, Jr. et al.

(10) Patent No.: US 7,176,324 B1
(45) Date of Patent: Feb. 13, 2007

(54) HEXAHYDROINDAN ACETAL AND KETAL COMPOUNDS AND THEIR USE IN PERFUME COMPOSITIONS

(75) Inventors: Anthony T. Levorse, Jr., Westfield, NJ (US); Brett D. Newirth, Atlantic Highlands, NJ (US); Margaux Des Jardins, Highland Park, NJ (US); Robert P. Belko, Monroe, NJ (US); Michael G. Monteleone, Hazlet, NJ (US)

(73) Assignee: International Flavors & Fragrances Inc., New York, NY (US)

( * ) Notice: Subject to any disclaimer, the term of this patent is extended or adjusted under 35 U.S.C. 154(b) by 0 days.

(21) Appl. No.: 11/314,304

(22) Filed: Dec. 21, 2005

(51) Int. Cl.
 *C07D 307/00* (2006.01)
 *C07C 41/00* (2006.01)
 *A61K 7/46* (2006.01)
 *C11D 3/50* (2006.01)

(52) U.S. Cl. .......................... 549/430; 568/670; 512/9; 512/13; 510/104

(58) Field of Classification Search ................ 549/430; 568/670; 512/9, 13; 510/104
 See application file for complete search history.

(56) References Cited

U.S. PATENT DOCUMENTS 4,211,674 A * 7/1980 Lenselink ...................... 512/9

\* cited by examiner

*Primary Examiner*—J. Parsa
(74) *Attorney, Agent, or Firm*—Elizabeth M. Quirk

(57) ABSTRACT

The present invention relates to hexahydroindan acetal and ketal compounds and their use as fragrance chemicals suitable for incorporation in fine fragrances, cosmetics, toiletries and related applications.

23 Claims, No Drawings

HEXAHYDROINDAN ACETAL AND KETAL COMPOUNDS AND THEIR USE IN PERFUME COMPOSITIONS

FIELD OF THE INVENTION

The present invention relates to new chemical entities and the incorporation and use of the new chemical entities as fragrance materials.

BACKGROUND OF THE INVENTION

There is an ongoing need in the fragrance industry to provide new chemicals to give perfumers and other persons ability to create new fragrances for perfumes, colognes and personal care products. Those with skill in the art appreciate how differences in the chemical structure of the molecule can result in significant differences in the odor, notes and characteristics of a molecule. These variations and the ongoing need to discover and use the new chemicals in the development of new fragrances allow perfumers to apply the new compounds in creating new fragrances.

SUMMARY OF THE INVENTION

The present invention provides novel chemicals, and the use of the chemicals to enhance the fragrance of perfumes, toilet waters, colognes, personal products and the like. In addition, the present invention is directed to the use of the novel chemicals to enhance fragrance in perfumes, toilet waters, colognes, personal products and the like.

More specifically, the present invention is directed to the Hexahydroindan Acetal and Ketal compounds, represented by the general formula set forth below:

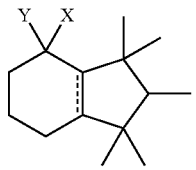

Formula I wherein the dotted line represents a possible double bond; X is H and Y is O—$CH_2$—O—$CH_2$—$R^1$ wherein $R^1$ is H, methyl and ethyl; and X and Y together may form a closed ring structure represented by

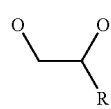

wherein R is H, methyl and ethyl.

Another embodiment of the invention is a method for enhancing a perfume composition by incorporating an olfactory acceptable amount of the compounds provided above.

These and other embodiments of the present invention will be apparent by reading the following specification.

DETAILED DESCRIPTION OF THE INVENTION

In a preferred embodiment of the invention, the novel compounds of the present invention are represented by the following structures:

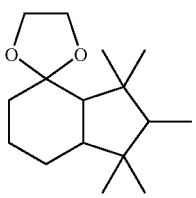

Structure I

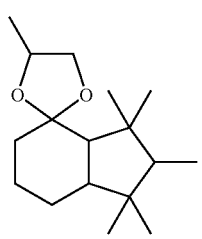

Structure II

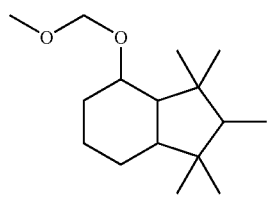

Structure III

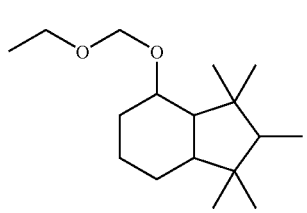

Structure IV

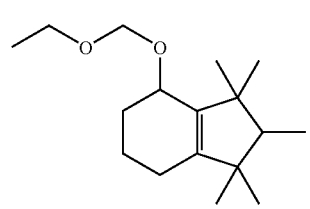

Structure V

Those with skill in the art will appreciate that the compound of Structure I 1,1,2,3,3-pentamethyl-octahydro-spiro [1,3-dioxolane-2,4-(4H)indene]; Structure II is 1,1,2,3,3,4- hexamethyl-octahydro-spiro[1,3-dioxolane-2,4-(4H) indene]; Structure III is 1,1,2,3,3-pentamethyl-octahydro-4-(methoxymethoxy)-1H-indene; Structure IV is 1,1,2,3,3-pentamethyl-octahydro-4-(ethoxymethoxy)-1H-indene and Structure V is 4-Ethoxymethoxy-1,1,2,3,3-pentamethyl-2,3,4,5,6,7-hexahydro-1H-indene.

The compound of Structure I may be prepared from the reaction of ethylene glycol and octahydro-1,1,2,3,3-pentamethyl-4H-indene-4-one, as disclosed in U.S. Pat. Nos. 5,227,367 5,733,866 and 5,665,698, by following the classic procedure used to protect ketone carbonyl compounds as described in Protective Groups in Organic Synthesis, Theodora W. Greene, Wiley publishing, see Example I below. A solution of the ketone, in this case octahydro-1, 1,2,3,3-pentamethyl-4H-indene-4-one and ethylene glycol in toluene is treated with a catalytic quantity of para-toluenesulfonic acid (p-TSA) and heated to reflux. Water generated as a by-product is removed from the reaction using a Dean-Stark trap. When the stoichiometric quantity of water has been recovered the reaction is finished. The acid catalyst is neutralized with an aqueous inorganic base like sodium hydroxide. The reaction mass is purified by fractional distillation giving the compound of structure I.

The compound of Structure II may be prepared from the reaction of 1,2-propylene glycol and octahydro-1,1,2,3,3-pentamethyl-4H-indene-4-one by following the classic procedure used to protect ketone carbonyl compounds as described for compound of Structure 1.

The compound of Structure III may be prepared from the reaction of octahydro-1,1,2,3,3-pentamethyl-1H-inden-4-ol and dimethoxy methane by following the procedure to prepare mixed acetals, see Example III below. A solution of octahydro-1,1,2,3,3-pentamethyl-1H-inden-4-ol, dimethoxy methane and toluene is treated with a catalytic quantity of a Lewis Acid, in this example boron trifluoride etherate complex. This mixture is heated to 100° C. and lites are recovered using a Dean-Stark trap. The reaction is neutralized with aqueous sodium carbonate then purified by fractional distillation giving the compound of Structure III.

The compound of Structure IV may be prepared from the reaction of octahydro-1,1,2,3,3-pentamethyl-1H-inden-4-ol and diethoxy methane by following the procedure to prepare mixed acetals as described for the compound of Structure III. We have discovered that the compounds have a warm amber character and a warm fruity character that are well suited for use as a fragrance ingredient.

The use of this compound is widely applicable in current perfumery products, including the preparation of perfumes and colognes, the perfuming of personal care products such as soaps, shower gels, and hair care products as well as air fresheners, candles and cosmetic products. The compound can also be used to perfume candles and cleaning agents, such as, but not limited to soaps, detergents, dishwashing materials, scrubbing compositions, window cleaners, fabric care products such as but not limited to fabric softeners, dryer sheets and the like.

In these preparations, the compound of the present invention can be used alone or in combination with other fragrance compositions, solvents, adjuvants and the like. Those with skill in the art will appreciate the nature and variety of the other ingredients that can be used in combination with the compound of the present invention.

Many types of fragrances can be employed in the present invention, the only limitation being the compatibility with the other components being employed. Suitable fragrances include but are not limited to fruits such as almond, apple, cherry, grape, pear, pineapple, orange, strawberry, raspberry; musk, flower scents such as lavender-like, rose-like, iris-like, and carnation-like. Other pleasant scents include herbal and woodland scents derived from pine, spruce and other forest smells. Fragrances may also be derived from various oils, such as essential oils, or from plant materials such as peppermint, spearmint and the like.

A list of suitable fragrances is provided in U.S. Pat. No. 4,534,891, the contents of which are incorporated by reference as if set forth in its entirety. Another source of suitable fragrances is found in *Perfumes, Cosmetics and Soaps*, Second Edition, edited by W. A. Poucher, 1959. Among the fragrances provided in this treatise are acacia, cassie, chypre, cyclamen, fern, gardenia, hawthorn, heliotrope, honeysuckle, hyacinth, jasmine, lilac, lily, magnolia, mimosa, narcissus, freshly-cut hay, orange blossom, orchid, reseda, sweet pea, trefle, tuberose, vanilla, violet, wallflower, and the like.

As used herein olfactory effective amount is understood to mean the amount of compound in perfume compositions the individual component will contribute to its particular olfactory characteristics, but the olfactory effect of the perfume composition will be the sum of the effects of each of the perfume or fragrance ingredients. Thus the compounds of the invention can be used to alter the aroma characteristics of the perfume composition by modifying the olfactory reaction contributed by another ingredient in the composition. The amount will vary depending on many factors including other ingredients, their relative amounts and the effect that is desired.

The level of compound of the invention employed in the perfumed article varies from about 0.005 to about 10 weight percent, preferably from about 0.1 to about 8 and most preferably from about 0.5 to about 5 weight percent. In addition to the compounds, other agents can be used in conjunction with the fragrance. Well known materials such as surfactants, emulsifiers, and polymers to encapsulate the fragrance can also be employed without departing from the scope of the present invention.

Another method of reporting the level of the compound of the invention in the perfumed composition, i.e., the compounds as a weight percentage of the materials added to impart the desired fragrance. The compounds of the invention can range widely from 0.005 to about 10 weight percent of the perfumed composition, and preferably from about 0.1 to about 5 weight percent. Those with skill in the art will be able to employ the desired level of the compound of the invention to provide the desired fragrance and intensity.

All U.S. patents and patent applications cited herein are incorporated by reference as if set forth herein in their entirety.

The following are provided as specific embodiments of the present invention. Other modifications of this invention will be readily apparent to those skilled in the art, without departing from the scope of this invention. Upon review of the foregoing, numerous adaptations, modifications and alterations will occur to the reviewer. These adaptations, modifications, and alterations will all be within the spirit of the invention. Accordingly, reference should be made to the appended claims in order to ascertain the scope of the present invention.

As used herein all percentages are weight percent. IFF is meant to be understood as International Flavors & Fragrances Inc.

EXAMPLE I

Preparation of 1,1,2,3,3-pentamethyl-octahydro-spiro[1,3-dioxolane-2,4-(4H)indene]

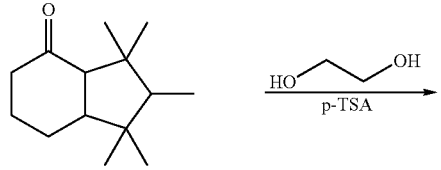

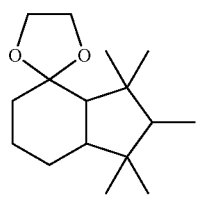

A reaction flask was charged with 500 g (2.4 mole) 1,1,2,3,3-pentamethyl-tetrahydro-4(3A)-indanone, as described in U.S. Pat. Nos. 5,227,367 5,733,866 and 5,665,698, 620 g (10 mole) ethylene glycol, 1 liter toluene, and 10 g para toluenesulfonic acid. The reaction mass was heated to 110° C. and water was collected in a Dean Stark trap. After 80 mL of water was recovered the reaction was cooled to 25° C. and acid catalyst was quenched with 20 g of 50% aqueous sodium hydroxide. The mass was transferred to a separatory funnel and water washed. The organic layer was separated and purified by fractional distillation. The procedure afforded a 76% yield (459 g) of 1,1,2,3,3-pentamethyl-octahydro-spiro[1,3-dioxolane-2,4-(4H)indene].

Bp 120° C. at 3 mmHg

NMR data: 0.61 ppm (s, 3H), 0.72–0.74 ppm (d, 3H, J=7.4 Hz), 0.82 ppm (s, 3H), 0.94 ppm (s, 3H), 0.94–1.02 ppm (m, 1H), 0.98 ppm (s, 3H), 1.12–1.18 ppm (m, 1H), 1.23 ppm (q, 1H, J=7.4 Hz), 1.38–1.46 ppm (m, 1H), 1.47–1.51 ppm (m, 1H), 1.56–1.59 ppm (m, 1H), 1.63–1.73 ppm (m, 1H), 1.76–1.81 ppm (m, 1H), 3.91–3.97 ppm (m, 2H), 3.98–4.05 ppm (m,2H).

Odor description: warm amber character

EXAMPLE 2

Preparation of 1, 1,2,3,3,4-hexamethyl-octahydro-spiro[1,3-dioxolane-2,4-(4H)indene]

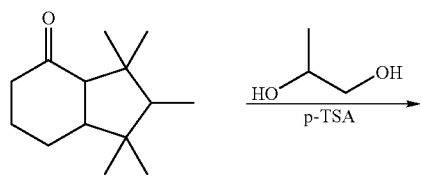

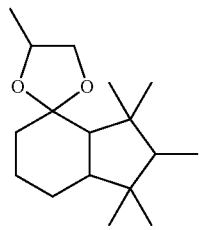

A reaction flask was charged with 618 g (2.9 mole) 1,1,2,3,3-pentamethyl-tetrahydro-4(3A)-indanone, 760 g (10 mole) propylene glycol, 1 liter toluene, and 10 g para toluenesulfonic acid. The reaction mass was heated to 112° C. and water was collected in a Dean Stark trap. After 133 mL of water was recovered the reaction was cooled to 25° C. and acid catalyst was quenched with 20 g of 50% aqueous sodium hydroxide. The mass was transferred to a separatory funnel and water washed. The organic layer was separated and purified by fractional distillation. The procedure afforded a 78% yield (600 g) of 1,1,2,3,3,4-hexamethyl-octahydro-spiro[1,3-dioxolane-2,4-(4H)indene].

Bp 134° C. at 3 mmHg

NMR data: 0.60 ppm (s, 3H), 0.71–0.73 ppm (m, 3H), 0.87 ppm (s, 3H), 0.92–0.96 ppm (m, 3H), 0.99–1.04 ppm (m, 3H), 1.10–1.8 ppm (m, 1H), 1.21–1.25 ppm (m, 1H), 1.26–1.34 ppm (m, 4H), 1.40–1.57 ppm (m, 3H), 1.61–1.78 ppm (m, 3H), 3.37–3607 ppm (m, 1H), 3.99–4.40 ppm (m,2H).

Odor description: warm fruity character

EXAMPLE 3

Preparation of 1,1,2,3,3-pentamethyl-octahydro-4-(methoxymethoxy)-1H-indene

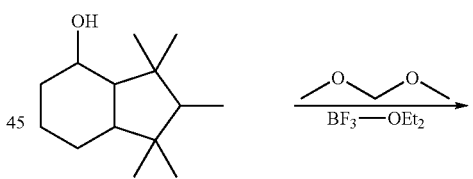

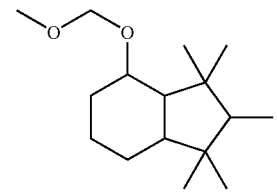

A reaction flask was charged with 300 g (1.4 mole) 1,1,2,3,3-pentamethyl-hexahydro-4-indanol, 306 g (4 mole) dimethoxymethane, 0.25 liter toluene, and 3 g boron trifluoride etherate complex. The reaction mass was heated to 100° C. and methanol and lite organics were collected in a Dean Stark trap (337 g recovered). After aging the reaction for 3 hrs the reaction was cooled to 25° C. and acid catalyst was quenched with 100 g of 10% aqueous sodium carbonate.

The mass was transferred to a separatory funnel and water washed. The organic layer was separated and purified by fractional distillation. The procedure affords a 55% yield (196 g) of 1,1,2,3,3-pentamethyl-octahydro-4-(methoxymethoxy)-1H-indene.

Bp 125° C. at 3 mmHg

NMR data: 0.61 ppm (s, 3H), 0.73–0.75 ppm (d, 3H, J=7.4 Hz), 0.81–0.83 ppm (m, 1H), 0.86 ppm (s, 3H), 0.92 ppm (s, 3H), 0.93–0.95 ppm (m, 1H), 0.97 ppm (s, 3H), 1.00–1.02 ppm (m, 1H), 1.13–1.19 ppm (m, 3H), 1.33–1.34 ppm (d, 1H, J=12.1 Hz, of d, J=10.2 Hz), 1.77–1.79 ppm (m, 1H), 2.18–2.21 ppm (m, 1H), 3.39 ppm (s, 3H), 3.43–3.48 ppm (t, 1H, J=10 Hz, of d, J=4.5 Hz), 4.68 ppm (d, 1H, J=6.7 Hz), 4.74 ppm (d,1H, J=6.7 Hz).

Odor description: warm amber character

EXAMPLE 4

Preparation of 1,1,2,3,3-pentamethyl-octahydro-4-(ethoxymethoxy)-1H-indene

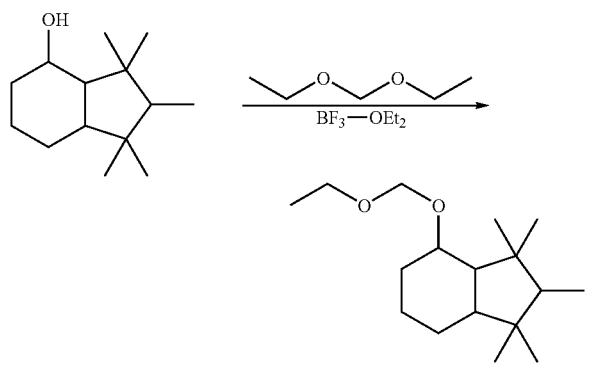

A reaction flask was charged with 300 g (1.4 mole) 1,1,2,3,3-pentamethyl-hexahydro-4-indanol, 258 g (2.5 mole) diethoxymethane, 0.25 liter toluene, and 5 g boron trifluoride etherate complex. The reaction mass was heated to 100° C. and methanol and lite organics were collected in a Dean Stark trap (190 g recovered). After aging the reaction for 2 hrs the reaction was cooled to 25° C. and acid catalyst was quenched with 100 g of 10% aqueous sodium carbonate. The mass was transferred to a separatory funnel and water washed. The organic layer was separated and purified by fractional distillation. The procedure afforded a 68% yield (256 g) of 1,1,2,3,3-pentamethyl-octahydro-4-(ethoxymethoxy)-1H-indene.

Bp 138° C. at 2 mmHg

NMR data: 0.61 ppm (s, 3H), 0.73–0.75 ppm (d, 3H, J=7.4 Hz), 0.85 ppm (s, 3H), 0.90–1.0 ppm (m, 2H), 0.91 ppm (s, 3H), 0.96 ppm (s, 3H), 1.13–1.22 ppm (m, 3H), 1.20 ppm (t, 3H, J=7.1 Hz), 1.29–1.33 ppm (m, 1H), 1.55.1.57 ppm (m, 1H), 1.77–1.79 ppm (m, 1H), 2.19–2.21 ppm (m, 1H), 3.45–3.47 ppm (m, 1H), 3.57–360 ppm (m, 1H), 3.66–3.70 ppm (m, 1H), 4.70 ppm (d,1H, J=6.9 Hz), 4.80 ppm (d,1H, J=6.9 Hz).

Odor description: warm amber character

EXAMPLE 5

Preparation of 4-Ethoxymethoxy-1,1,2,3,3-pentamethyl-2,3,4,5,6,7-hexahydro-1H-indene

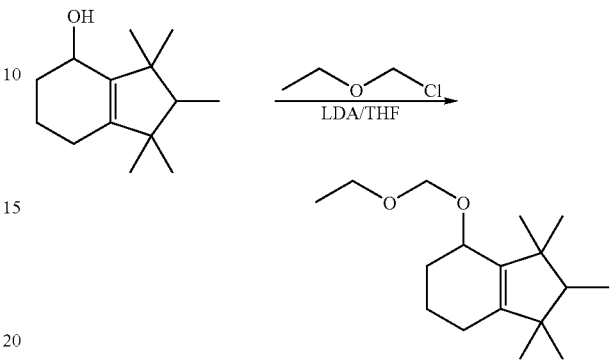

A reaction flask was charged with 100 mL of lithium diisopropyl amide (LDA, available from Aldrich Chemical Company) (2M in heptane/THF) and cooled to 0° C. 1,1,2,3,3-Pentamethyl-tetrahydro-4-indanol, as described in U.S. Pat. No. 3,636,165, 40 g (0.19 mole) was added in portions to the LDA solution. The reaction was aged 30 minutes then 18.5 g (0.2 mole) of ethoxy methyl chloride was added to the reaction mass at 0° C. The mass was allowed to exotherm to 25° C. The reaction was quenched with 100 g of 10% aqueous sodium carbonate. The mass was transferred to a separatory funnel and water washed. The organic layer was distilled. The procedure afforded a 60% yield (30 g) of 1,1,2,3,3-pentamethyl-hexahydro-4-(ethoxymethoxy)-1H-indene.

Bp 128° C. at 2 mmHg

NMR data: 0.85 ppm (d, 3H, J=7 Hz), 0.87 ppm (s, 3H), 0.91 ppm (s, 3H), 0.99 ppm (s, 3H), 1.05 ppm (s, 3H), 1.23 ppm (t, 3H, J=7 Hz), 1.52–1.45 ppm (m, 1H), 1.72–1.59 ppm (m, 2H), 1.87–1.79 ppm (m, 2H), 2.00–1.93 ppm (m, 2H), 3.72–3.61 ppm (m, 2H), 4.20 ppm (br s, 1H), 4.71 ppm (d, 1H, J=7 Hz), 4.82 ppm (d, 1H, J=7 Hz).

Odor description: warm amber character

What is claimed is:

1. A compound

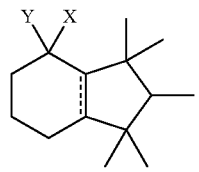

wherein the dotted line represents a potential double bond;

X and Y form a closed ring structure represented by

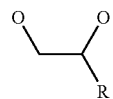

wherein R is H, methyl and ethyl; or
X is H and Y is O—CH$_2$—O—CH$_2$—R$^1$ wherein R$^1$ is H, methyl and ethyl.

2. The compound of claim 1 wherein X and Y form a closed ring structure represented by

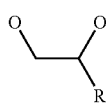

wherein R is H.

3. The compound of claim 1 wherein X and Y form a closed ring structure represented by

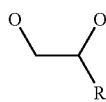

wherein R is CH$_3$.

4. The compound of claim 1 wherein X is H and Y is O—CH$^2$—O—CH$_2$—R$^1$ wherein R$^1$ is H.

5. The compound of claim 1 wherein X is H and Y is O—CH$^2$—O—CH$_2$—R$^1$ wherein R$^1$ is CH$_3$.

6. The compound of claim 1 wherein the dotted line represents a double bond and X is H and Y is O—CH$^2$—O—CH$_2$—R$^1$ wherein R$^1$ is CH$_3$.

7. A method of improving, enhancing or modifying a fragrance formulation through the addition of an olfactory acceptable amount of the compound of claim 1.

8. The method of claim 7 wherein the fragrance is incorporated into a product selected from perfumes, colognes, toilet waters, cosmetic products, personal care products, fabric care products, cleaning products and air fresheners.

9. The method of claim 8 wherein the cleaning product is selected from the group consisting of detergents, dishwashing compositions, scrubbing compounds and window cleaners.

10. The method of claim 7, wherein the amount incorporated into a fragrance is from about 0.005 to about 10 weight percent.

11. The method of claim 7, wherein the amount incorporated into a fragrance is from about 0.5 to about 8 weight percent.

12. The method of claim 7, wherein the amount of incorporated into a fragrance is from about 1 to about 7 weight percent.

13. A fragrance formulation containing an olfactory effective amount of the compound of claim 1.

14. A fragrance product containing a compound of claim 1.

15. A composition comprising a compound with the formula

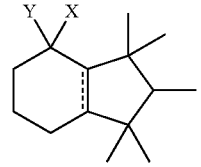

wherein the dotted line represents a potential double bond;
X and Y form a closed ring structure represented by

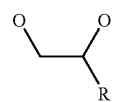

wherein R is H, methyl and ethyl; or
X is H and Y is O—CH$_2$—O—CH$_2$—R$^1$ wherein R$^1$ is H, methyl and ethyl.

16. A method of improving, enhancing or modifying a fragrance formulation through the addition of an olfactory acceptable amount of the compound of claim 15.

17. The method of claim 16 wherein the fragrance is incorporated into a product selected from perfumes, colognes, toilet waters, cosmetic products, personal care products, fabric care products, cleaning products and air fresheners.

18. The method of claim 17 wherein the cleaning product is selected from the group consisting of detergents, dishwashing compositions, scrubbing compounds and window cleaners.

19. The method of claim 16 wherein the amount incorporated into a fragrance is from about 0.005 to about 10 weight percent.

20. The method of claim 16 wherein the amount incorporated into a fragrance is from about 0.5 to about 8 weight percent.

21. The method of claim 16 wherein the amount of incorporated into a fragrance is from about 1 to about 7 weight percent.

22. A fragrance formulation containing an olfactory effective amount of the compound of claim 15.

23. A fragrance product containing a compound of claim 15.

* * * * *